United States Patent
Brady

(10) Patent No.: US 7,605,593 B2
(45) Date of Patent: Oct. 20, 2009

(54) METHOD AND APPARATUS FOR DETECTING INCONSISTENCIES IN CURED RESIN STRUCTURES

(75) Inventor: Steven K. Brady, St. Louis, MO (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 11/654,094

(22) Filed: Jan. 16, 2007

(65) Prior Publication Data

US 2008/0169828 A1 Jul. 17, 2008

(51) Int. Cl.
G01R 27/26 (2006.01)
(52) U.S. Cl. ............... 324/675; 324/655; 324/663; 73/780
(58) Field of Classification Search .......... 324/675
See application file for complete search history.

(56) References Cited

U.S. PATENT DOCUMENTS

| | | | |
|---|---|---|---|
| RE30,183 E * | 1/1980 | Popenoe ............ | 73/761 |
| 4,236,109 A * | 11/1980 | Ingle, Jr. ............ | 324/690 |
| 6,438,497 B1 * | 8/2002 | Mansky et al. ............ | 702/22 |
| 6,575,041 B2 * | 6/2003 | Schwarz et al. ............ | 73/780 |
| 6,774,643 B2 * | 8/2004 | Magill ............ | 324/663 |
| 2002/0158711 A1 * | 10/2002 | Groves et al. ............ | 333/174 |
| 2005/0229710 A1 * | 10/2005 | O'Dowd et al. ............ | 73/718 |

FOREIGN PATENT DOCUMENTS

WO PCT/US2007/022236 10/2007

OTHER PUBLICATIONS

King, R.J., "On-line Industrial Applications of Microwave Moisture Sensors", Sensors Update, vol. 7, 2000, pp. 109 to 170.*
Knochel, R., "Technology and Signal Processing of Dielectrometric Microwave Sensors for Industrial Applications", Transactions of The Metal Finishers Association of India, XX, vol. 7, 2000, pp. 65 to 105.*

* cited by examiner

Primary Examiner—Timothy J Dole
Assistant Examiner—Benjamin M Baldridge
(74) Attorney, Agent, or Firm—Tung & Associates

(57) ABSTRACT

Inconsistencies in a resin-based part are detected using a capacitive coupling probe having a tuned circuit and an impedance matching element. An alternating electric field produced by the probe penetrates the part. Inconsistencies in the resin part result in changes in the resonance of the circuit which are detected by a network analyzer.

14 Claims, 2 Drawing Sheets

METHOD AND APPARATUS FOR DETECTING INCONSISTENCIES IN CURED RESIN STRUCTURES

TECHNICAL FIELD

This disclosure generally relates to nondestructive testing and inspection techniques, and deals more particularly with a method and apparatus for detecting inconsistencies in cured resins and parts incorporating resins.

BACKGROUND

Composite material has a life cycle much like other materials. Inspection is part of the process used to track the condition of composite materials during its life cycle.

Inconsistencies in the resin of a composite structure may be difficult to detect using nondestructive testing without accompanying inconsistencies in the fibers of the composite. Inconsistencies in the resin of a composite structure may be caused by many sources including, but not limited to, exposure to high temperature for short time periods or moderate temperatures for long periods, lightning strikes and electrical arcing.

At present, there are no approved nondestructive test methods to assess inconsistencies in the resin of composites, particularly thermally induced resin inconsistencies.

The alteration of the composite structure may not be visible to the human eye. Accordingly, in order to determine whether a composite structure or part may have been subjected to excessive thermal loads, it was necessary to cut sample plugs or sections from regions of the structure or part suspected of having undergone alteration. The material samples were subjected to any of several testing techniques, such as thermal mechanical analysis (TMA) or differential scanning calorimetry (DSC). The removal of sample plugs for analysis was a time consuming and destructive process, which, in the case of commercial aircraft operations, increased maintenance costs and cycle times at maintenance facilities.

Nondestructive testing techniques employing an inductive probe have been developed to inspect the mechanical properties of a composite material structure. Inductive-type probes rely on inductive (magnetic) coupling with the composite material in order to assess the mechanical properties of the material. Some composite material structures incorporate an electromagnetic shielding layer (or layers) near one face which is used to help protect an aircraft against lightning strikes. Inductive coupling probes suffer signal-to-noise losses when inspecting composite structures through electromagnetic shielding layers which act to divert circulating eddy currents so that the currents cannot adequately interact with the resin matrix.

Accordingly, there is a need for a method and apparatus for nondestructively inspecting carbon fiber reinforced resin composite structures which overcome the problem discussed above. Embodiments of the disclosure are directed toward satisfying this need.

SUMMARY

According to one embodiment of the disclosure, an apparatus is provided for detecting inconsistencies in a resin-based structure, comprising a circuit including a capacitive probe producing an electric field coupled with material, and an analyzer for analyzing the response of the circuit to changes in the electric field resulting from the detection of inconsistencies in the resin. The circuit may be a tuned resonant circuit that includes a first variable inductor for tuning the circuit and a second variable inductor for impedance matching the circuit with the analyzer. The capacitive probe may include first and second sets of substantially coplanar, spaced apart conductors forming a capacitor. The first and second sets of conductors may include interlaced conductive fingers formed on a circuit board contained within a probe housing that holds the board in space relationship to the resin-based structure.

According to another embodiment, apparatus is provided for detecting variations in a carbon fiber reinforced resin composite material part. The apparatus may comprise: a surface capacitor generating an electric field penetrating the part; a circuit coupled with the surface capacitor and having electrical characteristics that change in response to changes in the electric field; and, an analyzer for analyzing changes in the electrical characteristics of the circuit. The surface capacitor may include a set of interlaced electrical conductors, wherein the electrical field is generated by surface effects between the conductors. The surface capacitor may be mounted on a support that holds the surface capacitor in spaced relationship to the surface of the part. The circuit may be a tuned resonant circuit that includes a variable circuit element for tuning the circuit. The circuit and surface capacitor are contained within a housing that is moveable across a surface of the part in order to scan the part for inconsistencies.

In accordance with a further embodiment, a method is provided for detecting variations in a woven fiber reinforced resin part. The method comprises the steps of: capacitively coupling a tuned resonant circuit with the part, variations in the part's resin causing changes in the resonance of the tuned circuit; and, analyzing changes in the resonance of the tuned circuit. The tuned resonant circuit may be coupled with the resin by moving a capacitor over a surface of the part. The method may further include applying an alternating frequency signal to the tuned circuit and generating an electric field using the alternating frequency signal. The electric field may be used to penetrate the part and interact with the resin.

In accordance with still another embodiment, a method is provided of detecting inconsistencies in a resin part containing conductive reinforcement fibers. The method may comprise the steps of: penetrating the part with an electric field; and, sensing changes in the electric field caused by inconsistencies in the part. The method may further include the steps of generating the electric field using a surface capacitor, and moving the surface capacitor across the surface of the part. Changes in the electric field may be sensed by measuring changes in the resonance of an electrical circuit.

The disclosed embodiments allow nondestructive inspection of reinforced and non-reinforced resin-based structures, including those containing conductive materials providing lightning strike protection. Inconsistencies, variations and alterations of the structure may be detected in spite of the presence of any conductive elements that may be embedded in the structure. Nondestructive inspection of composite structures can be quickly performed by maintenance personnel in the field to detect inconsistencies in the structure that are not visible to the human eye.

These and further features, aspects and advantages of the embodiments will become better understood with reference to the following illustrations, description and claims.

BRIEF DESCRIPTION OF THE ILLUSTRATIONS

DETAILED DESCRIPTION

Referring concurrently to FIGS. 1-4, a method and apparatus are provided for performing nondestructive inspection of resin-based material, such as a composite structure 12. The composite structure 12 may comprise a discrete part, or a portion of a larger structure such as, but not limited to, a beam, a frame, a stringer, super structure or skin of an aircraft, for example.

The composite structure 12 may include a plurality of plies 14 of a fiber reinforced resin matrix in which the fiber reinforcement comprises strands or a woven or knitted fabric of reinforcement fibers that function to reinforce the resin matrix. The orientation of the fibers in the plies 14 is typically arranged in alternating directions in order to maximize the mechanical strength of the composite structure 12. The reinforcement fibers may be, without limitation, a carbon based material or other material. The resin matrix may comprise, without limitation, a synthetic resin such as epoxy.

The composite structure 12 may include one or more layers 50 containing electrical conductors that function to protect the aircraft against the effects of direct lightning strikes. The conductive layer 50 forms a circuit that conducts current from a lightning strike location, in order to dissipate energy and minimize strike-induced inconsistencies. The composite structure 12 may include a variety of other embedded conductive elements such as the previously described carbon fibers which are bound within a resin matrix.

The composite structure 12 may contain any of a variety of inconsistencies in its constituent materials. These inconsistencies may include undesirable material properties, structural features or anomalies created either at the time of manufacture of the composite structure 12, or after the time of manufacture as a result of in-service operating conditions. "Inconsistencies", as the term is used in the appropriate context throughout this disclosure, refers to the difference between one or more measured characteristics of a composite structure that has been unaffected by exposure to external factors (including thermal loads, structural loads, oxidation, lightning or electrical arcing) with the same one or more measured characteristics of a composite structure that has been affected by exposure to the external factors.

Figure 1:
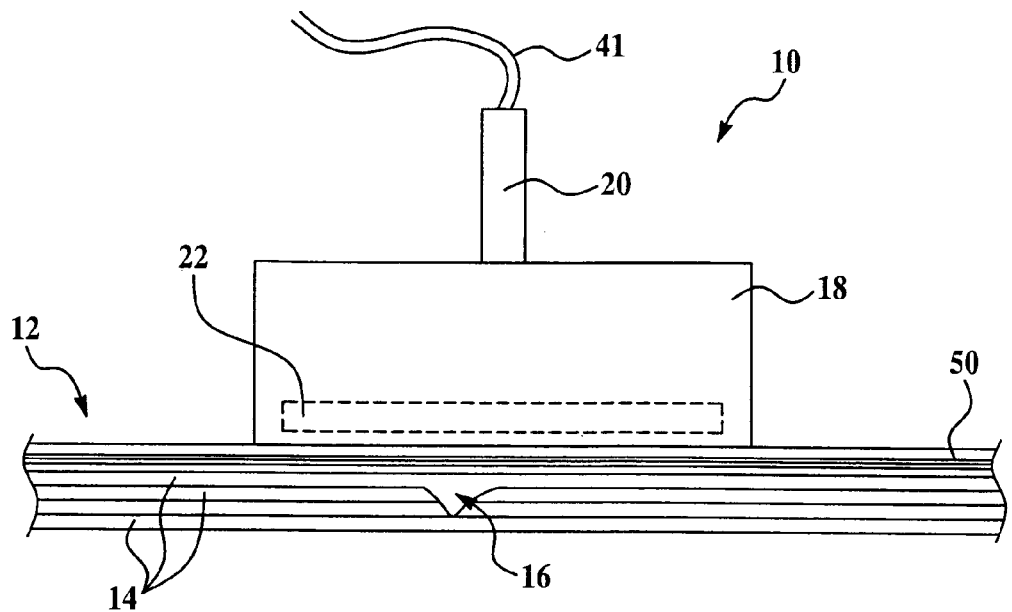
FIG. 1 is a side elevation illustration of apparatus for detecting inconsistencies in resin-based parts, shown in operative relationship to a composite structure containing an inconsistency.
Figure 2:
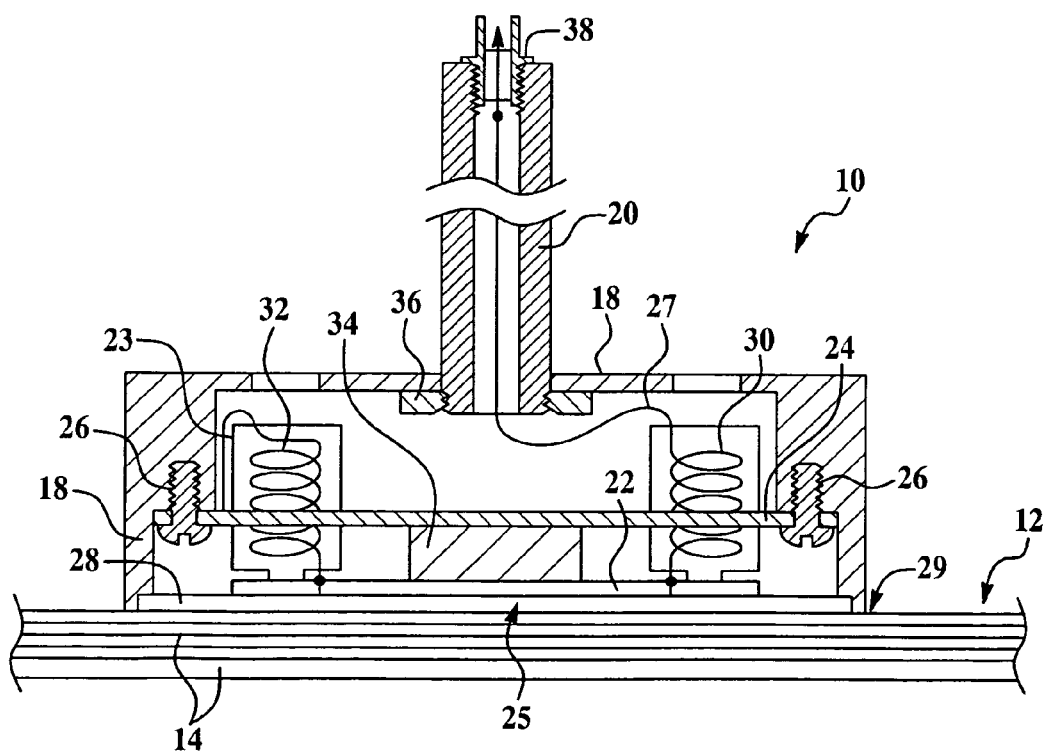
FIG. 2 is a cross sectional illustration of the apparatus shown in FIG. 1.

The detection of inconsistencies may be of interest to maintenance personnel in determining whether certain parts of an aircraft may require rework or replacement of parts. One such inconsistency 16 is shown in FIG. 1, on an exaggerated scale, wherein part of the resin matrix forming one of the layers 14 has been deformed or melted as a result of operating conditions such as excessive heat. Inconsistency 16 may also be a delamination or a void, to name a few. It should be noted here that although the inconsistency 16 is depicted as being physical in nature in FIG. 1 for ease of discussion, significant thermally-induced inconsistencies may not be manifested as physical changes, but rather may comprise chemical changes in the resin. In accordance with the present embodiment, the inconsistency 16 may be detected using a probe 10.

The probe 10 includes an outer housing 18 formed of a rigid, conductive material such as aluminum having a tube-like handle 20 passing through an opening (not shown) in the housing 18 and secured by any suitable means, such as the nut 36. A bracket 24 formed of rigid material such as copper is secured to the interior of the housing 18 by screws 26. A printed circuit board (PCB) 22 is mounted on the bracket 24 by means of a spacer block 34 formed of electrically insulating material. The lower face 25 of the PCB 22 is spaced slightly above the lower edge 29 of the housing such that when the probe 10 is placed on the surface of a composite structure 12 with the lower edges 29 resting on the surface of the structure 12, the PCB 22 is spaced slightly above the surface of the composite structure 12.

The opposite side of the PCB 22 has mounted thereon a variable coupling inductor 30, and a variable tuning inductor 32. A variable coupling capacitor (not shown) could be used in lieu of the coupling inductor 30. Tuning inductor 32 is connected to ground 33 via a lead 23 connected to one of the screws 26. The coupling inductor 30 has an electrical lead line 27 that passes through the hollow interior of the handle 20 and is connected to a coaxial cable 41 by means of a cable connector 38.

Figure 3:
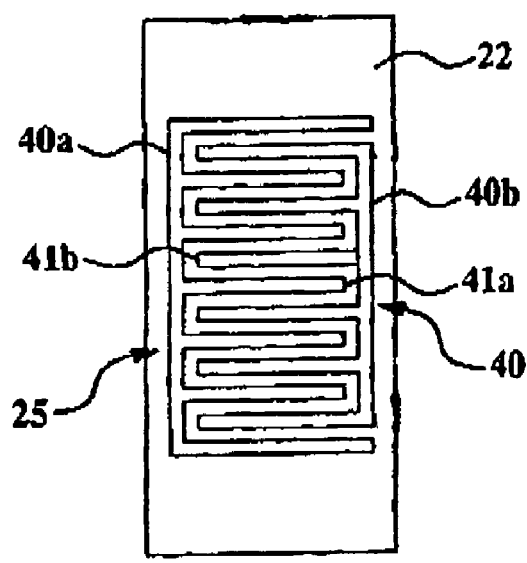
FIG. 3 is a plan illustration of a printed circuit board containing a surface capacitor forming part of the apparatus.

As best seen in FIG. 3 a printed circuit surface capacitor 40 is defined on the lower face 25 of the PCB 22. The surface capacitor 40 comprises first and second sets of interlaced conductive elements 40a, 40b which are spaced slightly from each other and lie in a plane spaced slightly above the surface of the composite structure 12 to be tested. A thin protective plate 28 is mounted on the bottom of the housing 18 to protectively cover the PCB 22. The plate 28 may be formed of any suitable material such as, without limitation, plastic or glass that allows transmission therethrough of an electric field. In lieu of the plate 28, a film (not shown) of insulating material may be deposited over the bottom of the PCB 22 to protect the surface capacitor 40.

Figure 4:
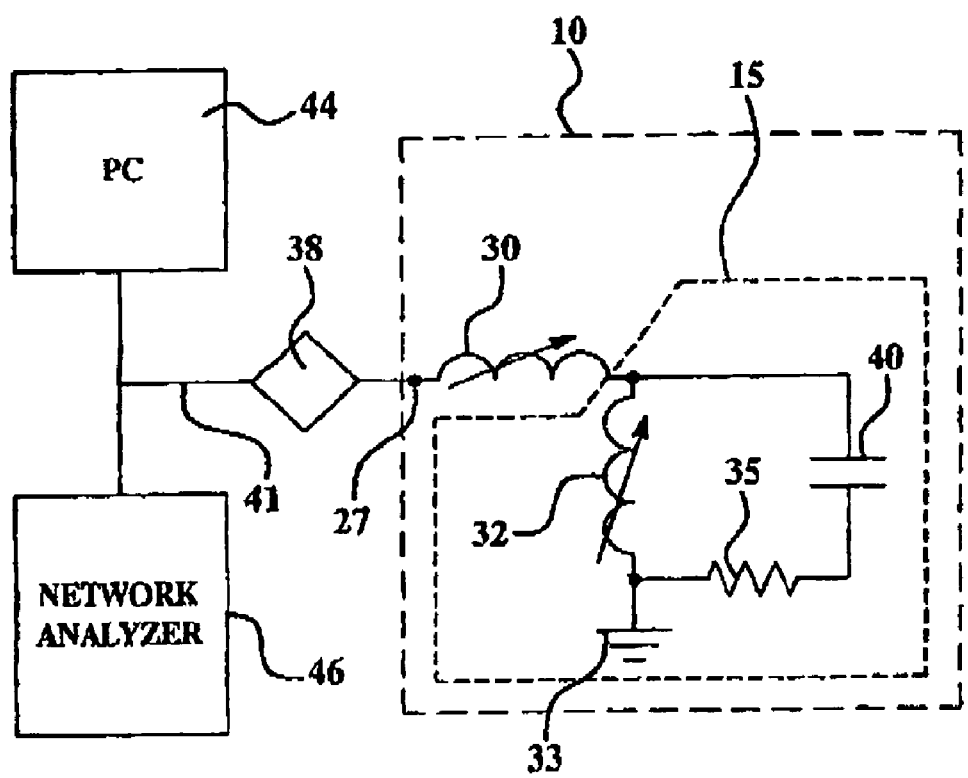
FIG. 4 is a simplified block and schematic illustration of an electrical circuit forming part of the apparatus.

The inherent resistance of tuning inductor 32 and surface capacitor 40 is represented as a collective resistance 35 in the circuit shown in FIG. 4. The tuning inductor 32, surface capacitor 40 and collective resistance 35 form LRC resonant circuit 15. The variable tuning inductor 32 allows the circuit 15 to be tuned to a particular resonant frequency. The variable coupling inductor 30 allows the circuit 15 to be impedance-matched to the network analyzer 46. The probe 10 is connected through a connection port 27 the BNC connector 38 and coaxial cable 41 to a network analyzer 46, and optionally, to a personal computer 44 or other computing device.

Network analyzer 46, which may comprise any of various commercially available, without limitation, devices such as a Hewlett Packard 8505A or 8753A network analyzer, functions to apply an alternating frequency signal to the circuit 15 and to observe the electrical impedance of circuit 15. This applied alternating signal results in alternating electrical fields being created between the neighboring fingers 41a, 41b of the interlaced conductors 40a, 40b of the surface capacitor 40. These alternating electric fields "bulge" off of the face of the PCB 22 due to edge effects, and penetrate the layers 14 of the composite structure 12. The alternating electric fields interact directly with the resin matrix in the composite structure 12. The frequency of the signal applied to the circuit 15 by the network analyzer 46 may be within a wide range of frequencies, depending on the particular application and the composition of the structure 12 being inspected. In connection with the inspection of carbon fiber reinforced epoxy structures, for example, frequencies in the range of 8 MHz to 18 MHz have been found to provide satisfactory results.

Inconsistencies 16 in the resin matrix or composite structure 12 create changes in the way the electric fields interact with the resin matrix. Specifically, it has been found that the dielectric lossiness of the epoxy resin matrix decreases monotonically as thermally induced inconsistencies increase. The response of the probe 10 therefore depends directly on the dielectric lossiness of the epoxy resin matrix in the composite structure 12. It should be noted here that although the illustrated embodiment has been described in connection with the inspection of a fiber reinforced resin structure, the embodiment may also be used to perform inspection of non-reinforced resin structures, and resin-based structures containing materials other than reinforcements.

The changes in the electric fields stemming from variations in the dielectric lossiness of the resin alters the resonance and impedance characteristics of the circuit 15, thereby evidencing the existence of a possible inconsistency. Changes in the resonance and impedance characteristics of circuit 15 may be detected by the network analyzer 46. The signals applied to the circuit 15 by the network analyzer 46, as well as changes in the resonance and impedance characteristics of the circuit 15 may be recorded and logged by the PC 44. The variable tuning inductor 32 allows the circuit 15 to be frequency tuned over a pre-selected range of frequencies. The variable coupling inductor 30 allows the circuit 15 to be impedance matched to the network analyzer 46, which as previously described, functions to excite the probe 10 and display the probe's impedance characteristics.

The direct interaction of the alternating electric fields generated by the probe 10 and the resin's dielectric lossiness mitigate some of the reduction in signal-to-noise experienced when inspecting through a lightning strike protection layer 50, compared to other inspection techniques, such as those employing an inductive coupling probe.

Although the embodiments of this disclosure have been described with respect to certain exemplary embodiments, it is to be understood that the specific embodiments are for purposes of illustration and not limitation, as other variations will occur to those of skill in the art.

What is claimed is:

1. Apparatus for detecting inconsistencies in a resin material, comprising:
    a tunable resonant circuit including a capacitive probe producing an electric field coupled with the resin material, said capacitive probe adapted to moveably operate in spaced relationship from a surface of said material to capacitively couple said electric field with said material while said capacitive probe is moving over said surface, wherein said capacitive probe comprises a surface capacitor including a set of substantially coplanar interlaced electrically conductive fingers; and,
        an analyzer for analyzing the response of the circuit to changes in the electric field resulting from the detection of inconsistencies in the resin material.

2. The apparatus of claim 1, wherein the tunable resonant circuit includes a variable inductor for tuning the tunable resonant circuit.

3. The apparatus of claim 1, further comprising a circuit board, and wherein a first set and a second set of conductors are formed on the circuit board, said first and second sets of conductors comprising the surface capacitor including a set of substantially coplanar interlaced electrically conductive fingers.

4. The apparatus of claim 1, further comprising a housing, and wherein the probe is held within the housing in said spaced relationship to the resin material.

5. Apparatus for detecting inconsistencies in a carbon fiber reinforced resin composite material part, comprising:
    a surface capacitor generating an electric field penetrating the carbon fiber reinforced resin composite material part, inconsistencies in the part causing changes in the electric field, said surface capacitor adapted to moveably operate in spaced relationship from a surface of said part to capacitively couple said electric field with said part while said surface capacitor is moving over said surface, wherein said surface capacitor comprises a set of substantially coplanar interlaced electrically conductive fingers;
    a tunable resonant circuit coupled with the surface capacitor and having electrical characteristics that change in response to changes in the electric field; and,
    an analyzer for analyzing changes in the electrical characteristics of the circuit.

6. The apparatus of claim 5, further comprising a support, wherein the surface capacitor is mounted on the support in said spaced relationship to the part.

7. The apparatus of claim 5, wherein the tunable resonant circuit includes a variable circuit element for tuning the circuit.

8. The apparatus of claim 5, further comprising a housing movable across a surface of the carbon fiber reinforced resin composite material part, and wherein the circuit and the surface capacitor are contained within the housing, the surface capacitor being mounted on the housing in said spaced relationship to the surface of the part.

9. A method of detecting inconsistencies in a resin-based part, comprising the steps of:
    (A) capacitively coupling a tuned resonant circuit with resin in the part, inconsistencies in the resin causing changes in the resonance of the tuned circuit, said tuned resonant circuit spaced apart from a surface of said part to capacitively couple en electric field with said part while said tuned resonant circuit is moving over said surface, wherein said tuned resonant circuit comprises a surface capacitor including a set of substantially coplanar interlaced electrically conductive fingers;
    (B) moving said tuned resonant circuit over said surface of said part; and,
    (C) analyzing the changes in the resonance of the tuned circuit.

10. The method of claim 9, wherein step (A) comprises the steps of:
    applying an alternating frequency signal to the tuned circuit; and,
    generating an electric field using the alternating frequency signal.

11. The method of claim 10, wherein step (A) includes penetrating the part with the electric field.

12. The method of claim 9, wherein step (A) includes penetrating the part with an electric field interacting directly with the resin in the part.

13. A method of detecting inconsistencies in a resin part containing conductive electrical elements, comprising the steps of:
    (A) penetrating the part with an electric field, said electric field generated by a tuned resonant circuit comprising a surface capacitor spaced apart from a surface of said resin part, said electric field capacitively coupling with said part while said surface capacitor is moving over said surface, wherein said surface capacitor comprises a set of substantially coplanar interlaced electrically conductive fingers;

(B) moving said surface capacitor over said surface of said part; and, (C) sensing changes in the electric field caused by inconsistencies in the part.

14. The method of claim 13, wherein step (C) includes measuring changes in the resonance of said tuned resonant circuit.

* * * * *